United States Patent [19]

Saltzstein et al.

[11] Patent Number: 5,217,020
[45] Date of Patent: Jun. 8, 1993

[54] BIOPHYSIOLOGICAL DATA ACQUISITION INCLUDING LEAD COMBINATION

[75] Inventors: William E. Saltzstein; Susan R. Hart; Peter M. Galen, all of McMinnville, Oreg.

[73] Assignee: Hewlett-Packard Company, Palo Alto, Calif.

[21] Appl. No.: 705,841

[22] Filed: May 28, 1991

[51] Int. Cl.[5] .............................................. A61B 5/0402
[52] U.S. Cl. ................................................... 128/696
[58] Field of Search ................................ 128/709-710, 128/696, 699; 364/413.06

[56] References Cited

U.S. PATENT DOCUMENTS 4,378,021  3/1983  Strand .................................... 128/709
4,981,141  1/1991  Segalowitz ........................... 128/696

Primary Examiner—Lee S. Cohen
Assistant Examiner—Jeffrey R. Jastrzab

[57] ABSTRACT

Method and apparatus for acquiring and processing EKG signals. A plurality of electrodes for measuring a patient's cardiac electrical signals provide analog electrode signals to an analog-to-digital converter via a plurality of electrode wires. The analog-to-digital converter converts the analog electrode signals to corresponding digital electrode signals which are then combined into combined signal leads.

4 Claims, 3 Drawing Sheets

BIOPHYSIOLOGICAL DATA ACQUISITION INCLUDING LEAD COMBINATION

TECHNICAL FIELD

This invention pertains to biophysiological data acquisition, and in particular to such data acquisition through sampled signals from a plurality of transducers.

BACKGROUND OF THE INVENTION

In the measurement of biophysiological data, for example, in electrocardiography, it is common to use electrodes attached to a patient to obtain signals which indicate physiological conditions and functions. The electrical signals present on the electrodes may be combined in various ways, that is "lead formation," resulting in signals called "leads."

Different systems of lead formation for electrocardiography have been developed, such as Einthoven, Frank and Cabrera, and are well known in the art. Systems have been developed for use in pediatrics, and all of these systems may be subdivided according to number of leads. Each of these different systems of lead formation present a heart's electrical signals in a different form, and in effect, provide a different view of the patient's heart.

Previously, resistor networks have been used to perform the lead formation. Such a hardware solution resulted in relative inflexibility in the lead combinations available. New or experimental lead combinations could not be used without altering the hardware. Furthermore, the precision and accuracy of lead combinations done by resistor networks are limited to the precision and accuracy of the resistors.

SUMMARY OF THE INVENTION

According to the present invention, a plurality of electrodes with respective electrode wires are attached to a patient for measuring biophysiological signals. As a primary feature of the present invention, the analog electrode signals present on the electrode wires are converted into digital form before they are combined into lead signals.

This lead combination may be performed by a general purpose programmable digital processor, or by a special purpose processor such as a digital signal processor.

As an advantage of the present invention, new or experimental lead formations may be programmed without any necessary change to the measuring systems's hardware.

As another advantage, the precision and accuracy of the biophysiological measurements are increased because no resistor networks are required.

As yet another advantage, different arbitrary lead formation systems may be used to enable the measuring system to operate in various roles, e.g., both as a electrocardiograph and as an electroencephalograph.

DETAILED DESCRIPTION OF THE INVENTION

Figure 1:
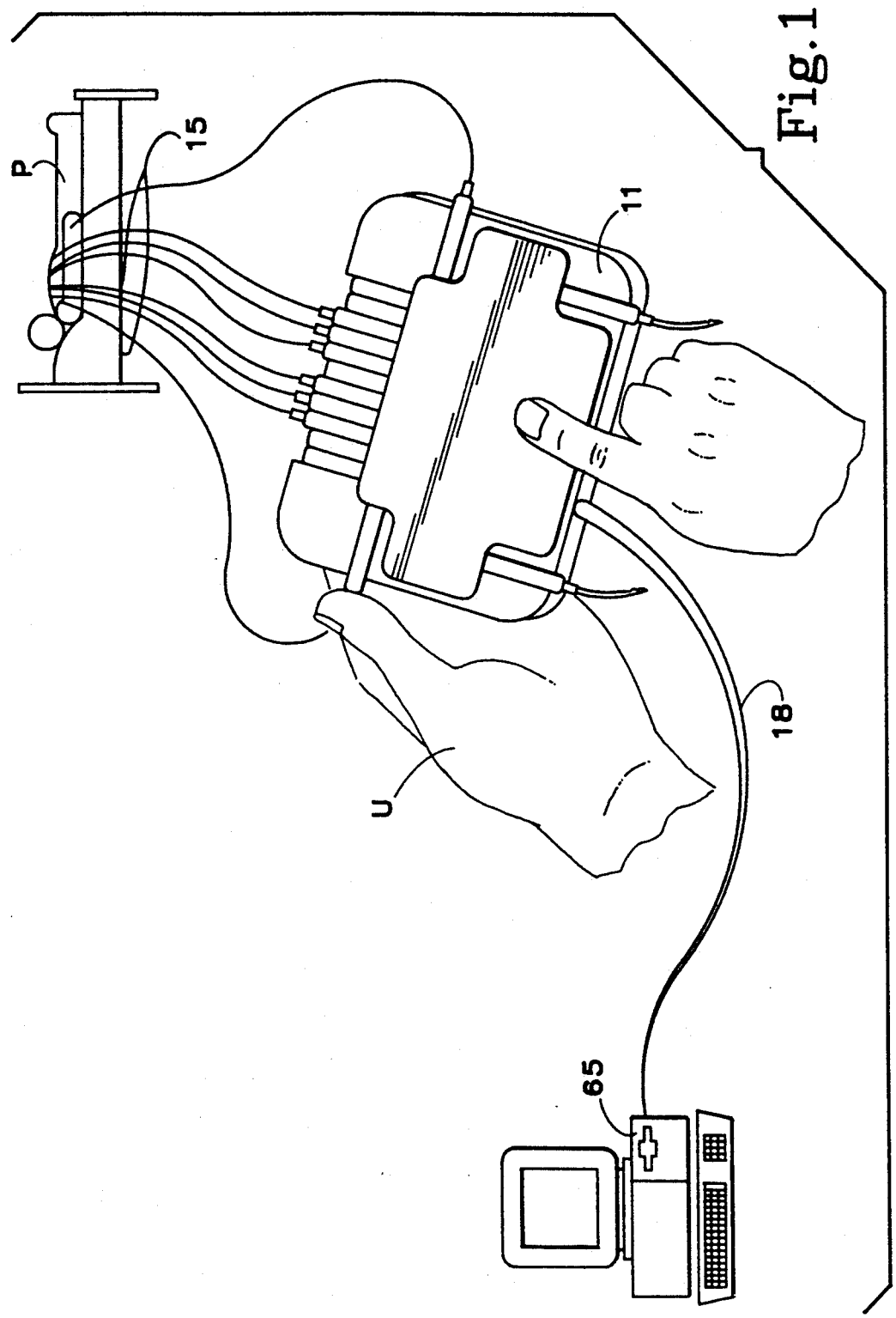
FIG. 1 is a plan perspective view of the portable data acquisition unit of the present invention.

With reference to FIG. 1, a portable data acquisition unit features a terminal block 11 with a plurality of electrode wires 15 extending to a patient P. Electrodes 16 are fixed to the patient for the purpose of gathering physiological data and converting the data to analog signals, such as skin potential. The electrodes generate signals which are transmitted along the electrode wires 15 back to the terminal block 11. The terminal block contains a time division multiplexer which is controlled by a sample order register. The terminal output is a sample signal on cable 18 to a remote host device 65 which may be computer or a cardiograph or similar device which also contains a CPU for communicating with the terminal block 11. Terminal block 11 is of a size which will readily fit in the hands of user U and may have signal condition indicating features which are the subject of co-pending applications.

Figure 2:
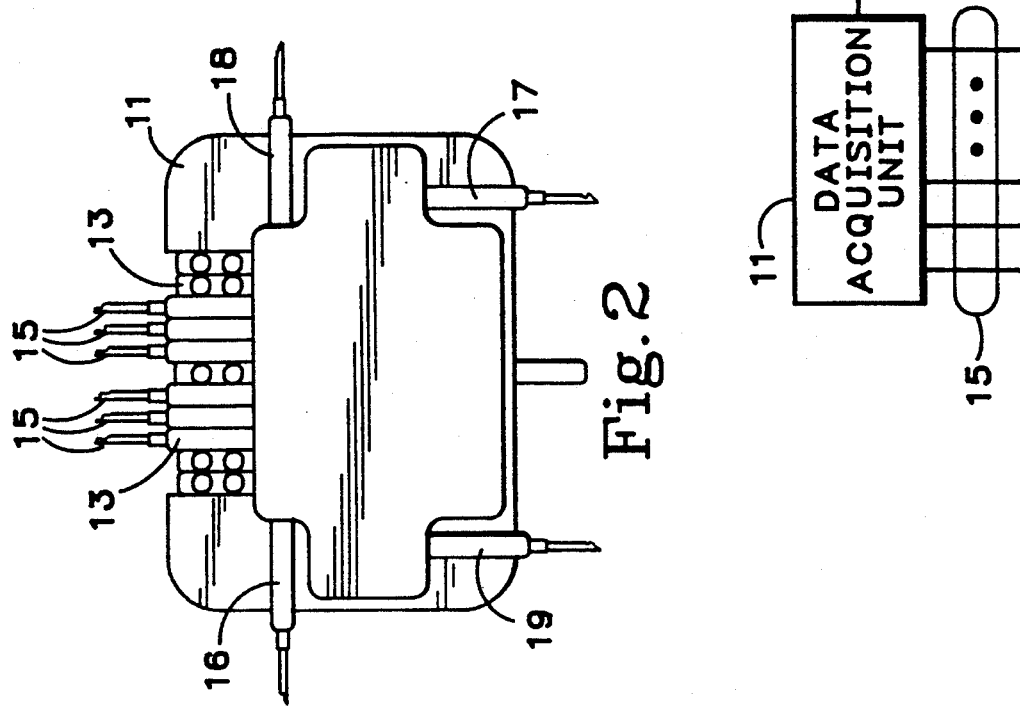
FIG. 2. is a top view of a data terminal used in the apparatus of FIG. 1.

In FIG. 2, the terminal block 11 is shown having a plurality of electrode wire contacts 13 along the periphery of the terminal block. The electrode wire contacts serve to terminate EKG electrode wires 15. The wire contacts may be plugs or receptacles which receive corresponding jacks associated with the EKG electrode wires. There are a total of fourteen wire contacts, including a right leg contact 19 and a left leg contact 17. Similarly, there is a right arm contact 16 as well as a left arm contact 18. The block is rectangular, having dimension of approximately six inches (15.24 cm) on a side and a depth of about one and a half inches (3.81 cm). Within the unit is a printed circuit board (not shown).

The electrical signals carried by electrode wires 15 are analog signals from a plurality of electrodes which measure electrical potential arising from contractions of the cardiac muscle. Alternatively, the electrode wires could carry signals from transducers which represent measurements of acoustic, ultrasonic, pressure, or almost any kind of a physical quantity. In other words, the data acquisition unit of the present invention is not restricted to use with EKGs, but may be used with any group of electrical signals to be transmitted to a remote location.

Figure 3:
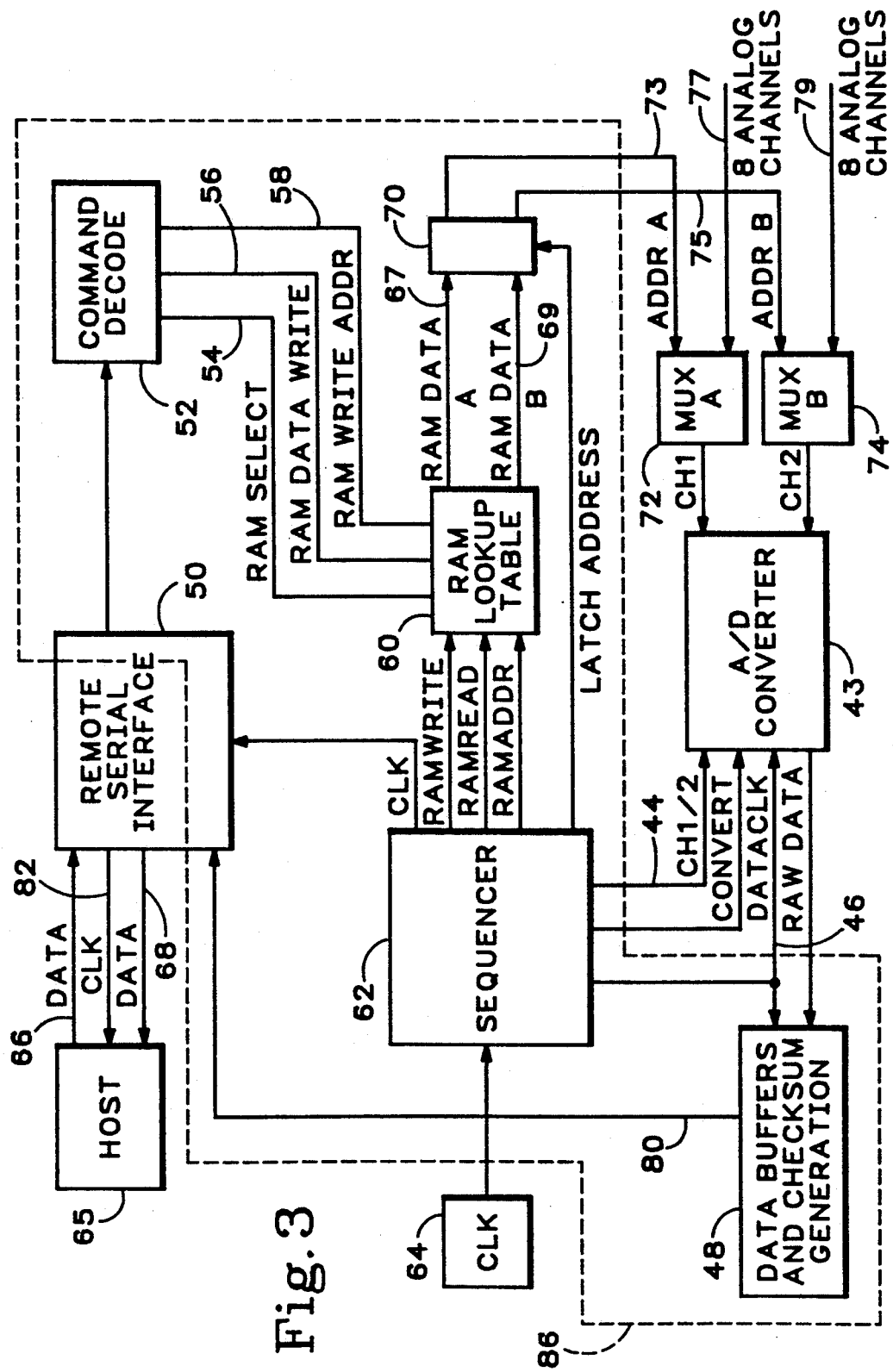
FIG. 3. is an electrical block diagram of the data terminal of FIG. 2.

With reference to the block diagram of FIG. 3, a RAM lookup table 60 may be seen which is connected to receive an input from the host 65 via data lines 66, while having an output to the multiplexers 72 and 74. Preferably, the sample order register is a volatile memory, such as a random access memory or a barrel register. The register is of a size sufficient for holding a list containing the sample order. For example, if sixteen electrical electrodes are to be used, a possible sample order might be as follows: 10, 1, 16, 2, 3, 4, 5, 15, 7, 12, 6, 9, 8, 13, 14, 11. Alternatively, in many cases data from only a few electrodes might be required and the sample order might be as follows: 3, 5, 4, 6, 11, 12, 3, 5, 4, 6, 11, 12, 3, 5, 4, etc. In either case, sixteen numbers consisting of the sample order for sixteen wires are loaded into the sample order register.

On power up of the circuit, host device 65, typically a cardiograph, transmits a sample order to a remote terminal. The remote terminal consists of all the blocks of FIG. 3, except for host 65. Transmission of the sample order is initiated by the remote terminal. A bit in the terminal-to-host status word is used to verify that the sample order is set after power on. If not set, the host transmits the sample order. The status word is transmitted along data line 68 from the remote serial interface 50. The communications protocol is such that seventeen words are transmitted every 250 microseconds. There are sixteen data words, plus a word that contains the checksum of the previous sixteen data words, along with the status information.

The sample order signal is transmitted to the command decode logic block 52 where the information is broken into a RAM select signal, transmitted along line 54; a RAM data write signal, transmitted along line 56; a RAM write address signal, transmitted along line 58. All signals are transmitted to the RAM lookup table 60. The lookup table 60 provides output signals along lines 67 and 69, representing requests for analog data at specified multiplexers in accord with the sample order. A sequencer 62, driven by clock 64, provides an address to the lookup table 60 and latch 70 and at the appropriate time, latches the sample order data from latch 70 to multiplexers 72 and 74 via the multiplexer address lines 73 and 75. The command decode logic 52, RAM lookup table 60 and the sequencer 62 form a sample order register means. The sample order is a list of numbers, written at appropriate addresses corresponding to analog data signals to be selected from multiplexers. The multiplexers 72 and 74 each receive eight channels of analog data coming from transducers collecting physiological data. These channels are represented by lines 77 connected to multiplexer 72 and lines 79 connected to multiplexer 74. In response to control signals from a remote host, a sample order register means writes, holds and reads a number sequence to be used for sampling electrode wires in multiplexers.

Signals from the multiplexers are transmitted to the analog-to-digital converter 43, which also receives the signal along line 44 for selecting between the two multiplexers. The logic signal for selecting the appropriate multiplexer is generated by sequencer 62 which is generating addresses for the RAM lookup table 60. Digital data from the electrode is transmitted along line 46 to data buffer 48 where data words and checksum signals are generated to form formatted data words using the protocol previously described. The formatted data words are transmitted along line 80 to the remote serial interface 50 for transmission to the host along line 68. A remote clock signal is also generated along line 82 for reading data at the host. There is bidirectional communication between the host and the remote terminal. The host may change the sample order at any time by providing a new list.

Since there are only sixteen analog channels, the same electrode may be sampled multiple times within the 250 microsecond period of each data work transmitted to the host. This rapid sampling allows an increase in the usable signal bandwidth, as well as selection and variation among electrodes to be sampled.

Host computer 65, contained in a cardiograph, is similar to a personal computer having a general purpose processor and an Industry Standard Architecture (ISA) buss. Analog-to-digital converter 43 and multiplexers 72 and 74 are commercial integrated circuits.

Since host device 65 establishes the sample order, the data acquisition unit which includes the sample order register is really a slave to the host device. This slave circuitry transmits whatever sample order is communicated from the host device. All of the functions indicated by the electrical blocks of FIG. 3 can be mounted on the small circuit card which fits into the data acquisition unit shown in FIG. 1.

Figure 4:
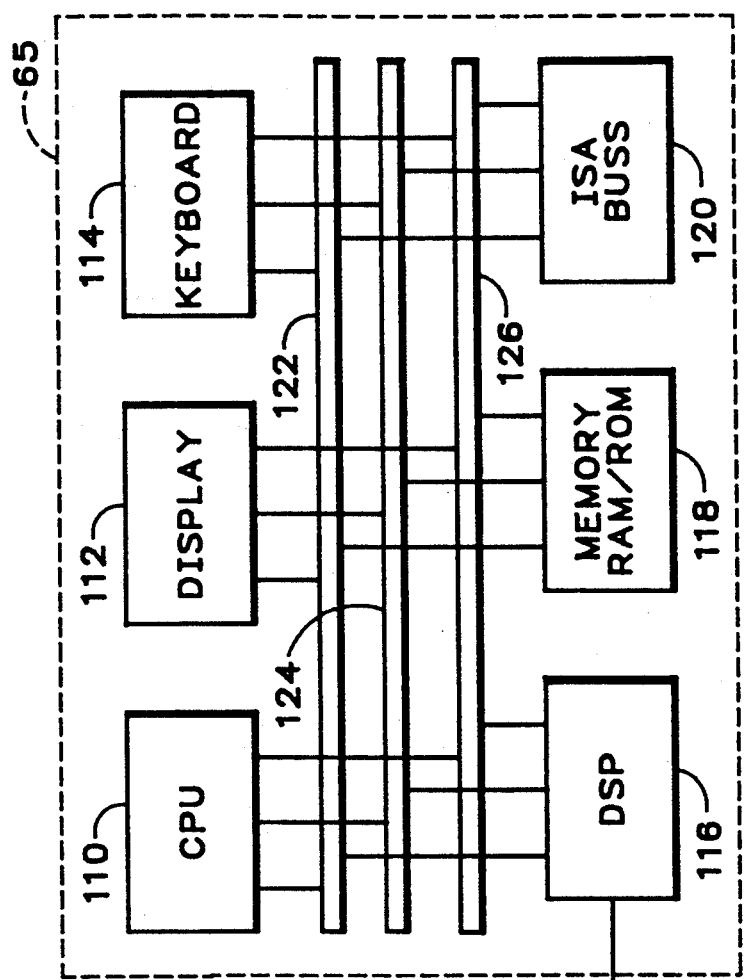
FIG. 4 is an electrical block diagram of the portable data acquisition unit connected to the host computer.

Referring now to FIG. 4, the portable data acquisition unit 11 is shown connected to the host computer 65. The host computer is arranged as is typical, having a central processing unit (CPU) 110, a display 112 for displaying text and graphical representations of acquired data, a keyboard 114 for input, memory (both random access memory, or RAM, and read only memory, or ROM) 118, and an industry standard buss 120. Also included is a digital signal processor 116 for processing the data acquired by the data acquisition unit 11 over the electrode wires 15. The elements in the host computer are interconnected as is well known in the art by a data buss 122, an address buss 124, and a control buss 126.

According to the present invention, the combining of the electrode signals into leads occurs after the signals have been converted to digital form. In the preferred embodiment, this combination is performed by the digital signal processor 116 during the filtration process. In a system without a digital signal processor, the lead formation may be done by the central processing unit 110.

In this preferred embodiment, the measurement system has been described as an electrocardiograph, or EKG. Such a limitation is not necessary as the advantages of the present invention may be used in other systems measuring biophysiological information. Also, the analog-to-digital converter has been described as located in a remote terminal not a part of the main EKG apparatus. It will be recognized by one of ordinary skill in the art that the analog-to-digital converter may be located in the main EKG to the same advantage.

Additional disclosure of other features and advantages of a data acquisition unit are disclosed in a co-pending patent application entitled "Portable Signalling Unit for an EKG" Ser. No. 07/529,015, filed May 25, 1990, now U.S. Pat. No. 5,085,224 which is hereby incorporated by reference.

What is claimed is:

1. An EKG data acquisition apparatus for acquiring a patient's electrical signals from a plurality of electrodes, comprising:
    (a) a plurality of electrode wires adapted to connect to the plurality of electrodes and transmit said electrical signals;
    (b) analog-to-digital converter means connected to said plurality of electrode wires for receiving said electrical signals and for converting said electrical signals to corresponding digital electrical signals; and
    (c) lead combination means for combining said digital electrical signals into leads.

2. The EKG data acquisition apparatus of claim 1, wherein said lead combination means comprises a programmable digital signal processor which combines said digital electrical signal into leads.

3. The EKG data acquisition apparatus of claim 1, wherein said lead combination means comprises a programmable general purpose digital processor which combines said digital electrical signals into leads.

4. An method of acquiring and processing EKG data, said method comprising:
    (a) measuring a patient's electrical signals, resulting in corresponding analog electrode signals;
    (b) converting said analog electrode signals to corresponding digital electrode signals; and
    (c) combining said digital electrode signals into combined signal leads.

* * * * *